United States Patent [19]

Ruiz

[11] 4,385,635
[45] May 31, 1983

[54] ANGIOGRAPHIC CATHETER WITH SOFT TIP END

[76] Inventor: Oscar F. Ruiz, 3655 Bay Homes Dr., Coconut Grove, Fla. 33133

[21] Appl. No.: 264,048

[22] Filed: May 15, 1981

Related U.S. Application Data

[63] Continuation-in-part of Ser. No. 143,891, Apr. 25, 1980, abandoned.

[51] Int. Cl.³ .............................................. A61B 6/00
[52] U.S. Cl. .................................... 128/658; 604/280
[58] Field of Search ............... 128/656, 658, 348–350, 128/214.4

[56] References Cited

U.S. PATENT DOCUMENTS

| | | | |
|---|---|---|---|
| 2,857,915 | 10/1958 | Sheudau | 128/658 |
| 3,612,038 | 10/1971 | Halligan | 128/658 |
| 3,618,614 | 11/1971 | Flynn | 128/658 |
| 3,935,857 | 2/1976 | Co | 128/658 |
| 4,015,601 | 4/1977 | Bokros | 128/348 |
| 4,117,836 | 10/1978 | Erickson | 128/658 |
| 4,184,497 | 1/1980 | Koloff et al. | 128/348 |
| 4,279,252 | 7/1981 | Martin | 128/658 |

*Primary Examiner*—Kyle L. Howell
*Assistant Examiner*—Nancy A. B. Swisher
*Attorney, Agent, or Firm*—John Cyril Malloy

[57] ABSTRACT

An angiographic catheter having a soft flexible, pliable leading tip zone consisting of elastomeric material wherein the tip zone of an axial length in the range between 1 and 10 millimeters, and wherein the catheter is composed of a main reinforced length and an intermediate zone between the tip zone and the main length, the main length being reinforced by an inner tube of a polyamide material and wherein the polyamide is tapered in the intermediate zone to provide a tapered reinforced section tapering distally and uniformly to zero at the tip zone. The catheter may be provided with perforations in a pattern as desired.

1 Claim, 2 Drawing Figures

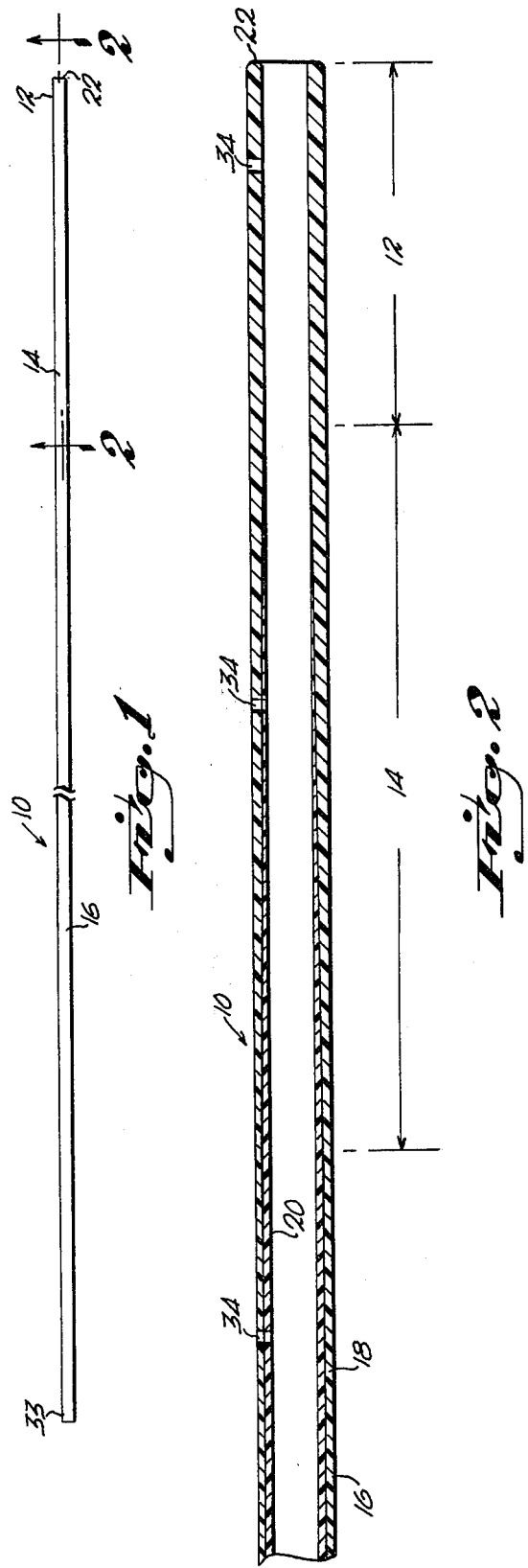

ANGIOGRAPHIC CATHETER WITH SOFT TIP END

This is a continuation-in-part of U.S. patent application Ser. No. 143,891 filed Apr. 25, 1980, now abandoned.

FIELD OF THE INVENTION

This invention relates to an angiographic catheter.

BACKGROUND OF THE INVENTION

In the past there have been various types of angiographic catheters. Generally speaking, such cathethers are utilized for diagnostic purposes. More particularly, such a catheter is inserted into an artery or vein and advanced in a generally axially direction through the vessel to a predetermined site as determined by an attending physician for the purpose of injecting radio opaque material. The radio opaque material should be injected under a relatively high pressure to achieve a relatively high concentration in a short period of time so that the images which are achieved in the conventional manner are as sharp as possible.

It will be appreciated by those in the art that such catheters must be quite rigid. This is required to be capable of advancement by pushing, to be susceptible to axial movements of adjustment and to resist twisting or torque forces. Such catheters must also be able to withstand a high bursting pressure while, at the same time, the tip should be as soft as possible so as not to cause injury to the interior wall of the vessel as it is advanced.

SUMMARY OF THE INVENTION

This invention is of an improved angiographic catheter having a soft non-traumatic tip zone with the required characteristics referred to above.

SUMMARY OF KNOWN PRIOR ART

In the prior art there are, for example, angiographic catheters have been utilized that are braided, that is, catheters which are reinforced with a steel wire mesh or Dacron reinforcing braid in order to accommodate high compressive forces, resistance to bursting, etc. as required to move it through a vein to a desired site and deliver radio opaque dye under relatively high pressures. There have also been other types of angiographic catheters, for example, two tubes, each of a different type of polyethylene and each of a different rigidity have been adhered together in coaxial relation.

Generally speaking, it is a recognized problem in this art to provide an angiographic catheter having a terminal end, or leading end, which is soft, so that it will not penetrate a vessel wall, traumatize the vessel, and which will be less likely to dislodge plaque from the interior wall of a vessel through which it is being advanced yet which is, nevertheless, reinforced so as to have a high bursting strength and be capable of resisting compressive forces so that it can be advanced and rotated as required in order to be utilized as described above.

OBJECTS OF THE INVENTION

It is a general object of this invention to provide an improved reinforced angiographic catheter having a relatively soft tip so as to be, generally speaking, non-traumatic.

It is also an object of this invention to provide an improved reinforced angiographic catheter having an exterior sleeve or surface of a soft elastomeric material and a relatively soft non-traumatic tip which is not reinforced.

It is another object of this invention to provide an angiographic catheter having a soft tip of a length between 3 and 7 millimeters and preferably about 5 millimeters which is non-reinforced and is of flexible, pliable, yieldable, bendable material.

If it a further object of this invention to provide an angiographic catheter wherein the overall length of the catheter is composed of an exterior sleeve of soft elastomeric material jacketing an inner reinforcing tube of a properly compounded polyamide material, such as nylon, and, which interior tube, adjacent, but not at, the terminal or leading end of the catheter tapers to zero, so that the distal end is of elastomeric material, such as urethane, constituting a soft tip.

It is another object of this invention, generally speaking, to provide an improved soft non-traumatic tipped angiographic catheter which is generally inexpensive to manufacture, which is capable of injecting radio opaque material under high pressure and which has relatively thin walls and which will not burst at pressures of up to about 1,200 psi or higher for the purposes which are set forth more fully hereinafter.

In accordance with these and other objects which will become apparent hereinafter, the instant invention will now be described with reference to the accompanying drawings of which:

DESCRIPTION OF THE DRAWINGS

FIG. 1 is a side view of the terminal end zone of an angiographic catheter in accordance with this invention; and FIG. 2 is an enlarged view of that portion of the catheter shown in FIG. 1 taken on the plane indicated by the arrowed lines designated by the numerals 2—2.

DESCRIPTION OF THE PREFERRED EMBODIMENT

Referring to the drawings the improved catheter is generally designated by the numeral 10. As seen in FIG. 2, it includes a soft tip or a terminal zone designated by the numeral 12, an intermediate zone 14, and a main fully reinforced length 16. Along the entire length there is a exterior jacket or sleeve designated by the numeral 18 of elastomeric material which is relatively soft, bendable, flexible and pliable. Within the main length of this jacket, as designated by the numeral 20, there is a reinforcing tube adhered to the inside diameter of the elastomeric jacket or sleeve. This inner tube is of a polyamide which provides rigidity, torque control, and may generally be described as being of high strength, so that, when the catheter is pushed axially, it will advance in response to the applied forces without collapsing and through it dye can be forced under high pressure without bursting the catheter.

Intermediate the terminal end zone 12 and the main length 16, there is an intermediate zone 14, see FIG. 2. In this intermediate zone, the jacket or exterior sleeve of elastomeric material is somewhat tapered, so that it is enlarged in cross-section at the distal portion of this zone, as compared to the proximal portion, while, correspondingly, the relatively rigid interior tube of reinforcing polyamid is tapered to providing an easy transition between the main fully reinforced length and the soft tip.

As is perhaps well known, the inside diameter of an angiographic catheter should be in the range of 0.020 inches to about 0.070 inches. This structure as described above accommodates such interior diameter while the outer circumference may be held to between 2 millimeters and 8 millimeters. It will be appreciated that this construction provides a relatively thin wall while maintaining a large lumen with high pressure bearing capability.

In the preferred embodiment shown, the intermediate zone designated by the numeral 14 is between 1 and 3 centimeters in length. In the preferred embodiment, throughout the intermediate zone, the taper of the reinforcing polyamide is uniform and goes to zero at the beginning of the tip zone 12, that is, it reaches zero thickness. In the intermediate zone, the sum of the wall thickness of the soft outer elastomeric material plus the wall thickness of the reinforcing material is about the same as that of the main length 16 and of the elastomeric tip 12, which is not reinforced; however, the latter may be somewhat thinner or thicker. The length of the tip zone 12 is preferably in the range of between 1 millimeter and 7 millimeters.

It will be appreciated that, if the terminal or leading end zone 22 were of generally high strength throughout its length, as the leading end or tip is advanced through a vessel, it might pierce or cause trauma to the interior wall of the vessel at a bend or curve. This construction provides a terminal end zone which is soft, bendable, flexible and pliable and which can be advanced readily and utilized in the manner described.

It is thus seen that there is provided a soft tip angiographic cathether which is able to withstand an interior bursting pressure of up to 1,200 pounds so that a high concentration of radio opaque material may be injected in a short time period and a clear picture taken for a diagnostic purpose by an attending physician. This is accomplished by the structure disclosed without the necessity of braiding or steel reinforcing wire mesh which have been utilized in the past. When such reinforcing braiding has been used in the past in order to achieve a somewhat softer tip zone some have become broken, dislodged or separated causing internal damages and had to be retrieved by a snare or surgically.

It will be understood that the proximal end 33 of the catheter is adapted in a conventional manner for connection to a standard Luer Lock or hub for introducing the dye from a source; and that a pattern of holes such as 34 may be provided as desired along the length or just at the tip or tip and intermediate zone.

While the instant invention has been shown and described herein in what is conceived to be the most practical and preferred embodiment, it is recognized that departures may be made therefrom within the scope of the invention, which is therefore not to be limited to the details disclosed herein but is to be accorded the full scope of the claims so as to embrace any and all equivalent apparatus and articles.

What is claimed is:

1. An angiographic catheter having a soft flexible pliable leading tip zone comprising urethane and forming a non-traumatic catheter tip, said tip zone being of an axial length in the range of between 1 and 7 millimeters, said catheter comprising a main reinforced length and an intermediate zone between the tip zone and the main length, said main length of said catheter including an inner tube of a polyamide jacketed by urethane, said intermediate zone comprising a tapered end zone of said inner tube of polyamide tapering to zero to provide decreasing stiffness between said main length and said tip zone and said intermediate zone is jacketed by urethane, said intermediate zone, said main length and said tip zone being of an overall wall thickness substantially common throughout the axial length of the tip zone, intermediate zone and adjacent main length, wherein a soft flexible pliable leading tip zone is provided and a relatively flexible intermediate zone is provided for said catheter.

* * * * *